US00PP12778P2

(12) United States Plant Patent
Kanno

(10) Patent No.: US PP12,778 P2
(45) Date of Patent: Jul. 16, 2002

(54) OSTEOSPERMUM PLANT NAMED 'KAKEGAWA AU3'

(75) Inventor: Masao Kanno, Chigasaki (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/658,458

(22) Filed: Sep. 8, 2000

(51) Int. Cl.[7] ..... A01H 5/00

(52) U.S. Cl. ..... Plt./360

(58) Field of Search ..... Plt./360

*Primary Examiner*—Bruce R. Campell
*Assistant Examiner*—Annette H. Para
(74) *Attorney, Agent, or Firm*—Rothwell, Figg, Ernst & Manbeck

(57) ABSTRACT

The present invention relates to a new and distinct variety of *Osteospermum fruticosum* (L.) Norl plant named 'Kakegawa AU3'. This new plant has a suitable form for pot culture and also possesses large red-purple flowers that stay open into the evening hours or under low light conditions.

1 Drawing Sheet

BACKGROUND OF THE INVENTION

The present invention relates to a new and distinct variety of the Compositae family. The new variety, a member of the species *Osteospermum fruticosum* (L.) Norl., named 'Kakegawa AU3'. This species is one of several species of Osteospermum that are commonly referred to as Cape Daisy.

The new variety originated as a first generation hybrid seedling following four generations of random intercrossing between population selections. All crosses were done at the Sakata Seed Corporation, Chogo Research Station in Chogo Prefecture, Japan. The objective of this breeding program was to develop plants with suitable form for pot culture that also possessed large flowers that would stay open into the evening hours. The flowers of *Osteospermum fruticosum* (L.) Norl. usually close under low light conditions, such as in the evening.

The original parent lines for the new variety were *Osteospermum fruticosum* (L.) Norl breeding lines 697 and 137, female and male respectively. These two lines were cross pollinated in 1991. From this hybridization several first generation seedlings were obtained and grown to mature, flowering plants. In 1992 six of these plant lines were selected due to their flowers staying open at low light levels. The six lines were intercrossed and the progeny grown to flowering, where selection and intercrossing of the selected lines was repeated. Flower size, ability to stay open in the evening and deep purple petal color was used as selection criteria. This procedure was continued until progeny from the 1995 crosses were ready to be evaluated. In April, 1996, one line was selected as 'Kakegawa AU3'. Further evaluation by the inventor during 1996 and 1997 demonstrated that the new variety's characteristics were firmly fixed and stable. Since this time the new variety has been trialed and vegetatively propagated at the Sakata Seed Corporation facility in Salinas, Calif. The new variety has been stable and fixed in this environment also.

The new variety has been observed under greenhouse and outdoor conditions in California and Japan. The phenotype of the new plant may vary somewhat with variations in temperature, day length, light intensity or soil media conditions. The observations noted below have been made using multiple 8 month old plants grown in Salinas, Calif. under the following conditions. Shoot tips were rooted in soil plug trays in August. After developing a root ball the plants were transplanted into six-inch diameter pots and grown outdoors through the winter to provide vernalization for flowering. In December, buds were pinched off to promote branching. Winter night temperatures averaged 40 to 50 degrees Fahrenheit. By May of the following year the plants were in full bloom. Average summer daytime temperatures in Salinas range from 60 to 75 degrees Fahrenheit depending on the month and the amount of coastal marine layer cloud cover.

BRIEF DESCRIPTION OF THE PHOTOGRAPHS

The accompanying color photographs illustrate the appearance the new variety, 'Kakegawa AU3'. The colors are representated as true as possible using conventional photographic procedures.

DETAILED DESCRIPTION OF THE NEW VARIETY

Figure 1:
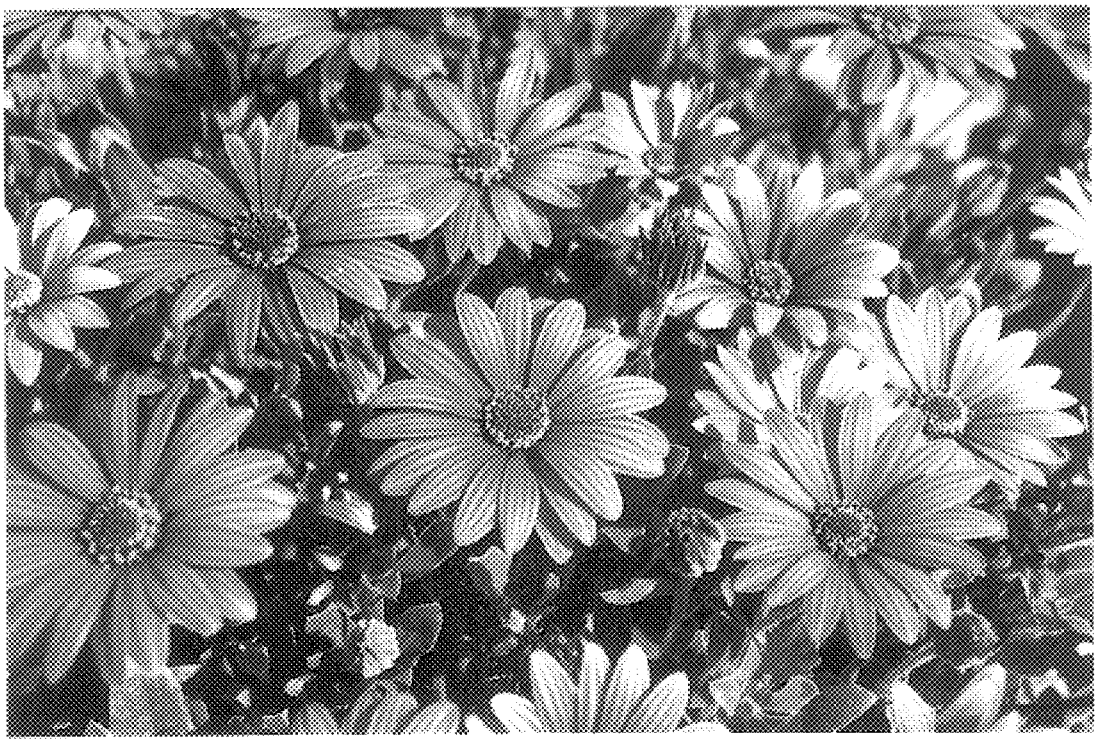
FIG. 1 is a close-up view of multiple blooms illustrating the petal color.
Figure 2:
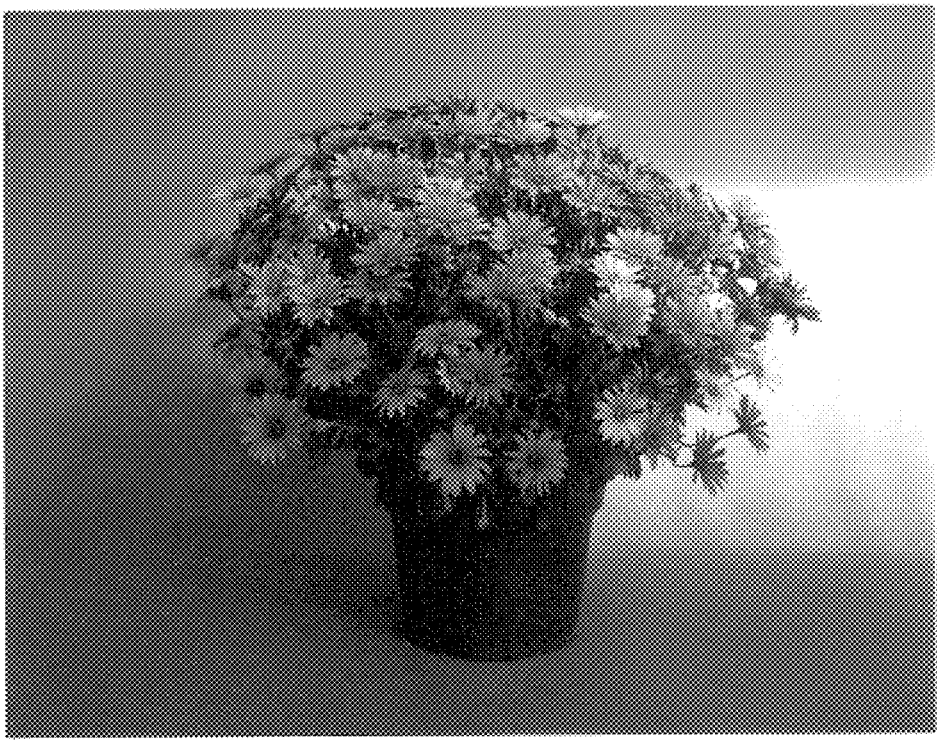
FIG. 2 is a view of the entire plant showing its form in pot culture when in full bloom.

The following traits and characteristics describe the new variety. Color references are made to The Royal Horticultural Society Colour Chart (R.H.S.), published by The Royal Horticultural Society of London, England, except where general terms of ordinary significance are used.

Classification

*Family.*—Compositae (Asteraceae).

*Genus and species.*—*Osteospermum fruticosum* (L.) Norl.

*Common names.*—African Daisy, Cape Daisy, Freeway Daisy.

*Cultivar name.*—'Kakegawa AU3'.

Parentage:

*Female and male parent.*—This variety is from unknown parents. The parental lines were the product of three generations of selection and intercrossing following the initial cross between breeding line 697 and breeding line 137.

Growth:
*Habit.*—Vigorous, well branched.
*Life cycle.*—Perennial.
Plant description:
*Height.*—37 cm to 42 cm.
*Width.*—40 cm to 50 cm.
*Form.*—Upright.
*Lastingness of florescence.*—7 days.
Stems:
*Stem color.*—RHS 144A (yellow green).
*Stem description.*—Strong, erect, herbaceous, glabrous.
*Stem diameter.*—3 mm to 4 mm.
*Internode length.*—0.8 cm to 1.0 cm.
Leaves:
*Leaf arrangement.*—Alternate; sessile.
*Leaf apex.*—Mucronate.
*Leaf base.*—Oblique.
*Leaf color.*—Upper RHS 137A (green); lower RHS 137D (green).
*Leaf edge.*—Slightly serrated.
*Leaf shape.*—Lanceolate.
*Leaf venation.*—Pinnate.
Flowers:
*Phyllaries.*—Arrangement — symmetrical; length 13 mm; width 1.5 mm; shape linear; apex acute; margin entire; texture pubescent; upper color RHS 137D (green); lower color RHS 138C (green).
*Corolla.*—Free.
*Flower diameter.*—5.5 cm to 6.0 cm.
*Flowering habit.*—Determinate.
*Fragrance.*—None.
*Inflorescence type.*—Solitary on terminal peduncles.
*Ovary.*—*Inferior.*
*Peduncle.*—Texture pubescent; length 3–6 cm; diameter 0.2 cm; color RHS 143C (green).
*Bud.*—Shape round, pointed at the top; length 1.3 cm; width 0.8 cm; color RHS 143C (green).
*Ray floret shape.*—Spatulate; apex obtuse; margin entire.
*Ray floret color.*—Dorsal surface of ray florets are RHS 71A (red-purple); ventral surface of ray florets is RHS 72C (red-purple); disk florets is RHS 89C (violet-purple).
*Ray floret size.*—2.5 cm to 3.0 cm in length; 0.6 cm to 0.7 cm in width.
*Ray floret number.*—21 to 22.
*Disc floret shape.*—Tubular.
*Disc floret size.*—5.0×0.7 mm.
*Disc floret number.*—55 per head.
*Propagation to bloom.*—18 to 20 weeks when rooted vegetative cuttings are transferred to a six-inch diameter pot in late Fall and given several weeks of below 50 degree Fahrenheit temperature prior to increasingly warmer spring weather.
Reproductive organ:
*Stigma.*—RHS N77A (purple).
*Style.*—RHS N81B (purple-violet).
*Anther.*—RHS N77A (purple).
*Filament.*—RHS N81B (purple-violet).
*Pollen color.*—RHS 17A (yellow-orange).
*Fruit and seed.*—Not produced.

DISEASE AND INSECT RESISTANCE

No known susceptibility to diseases or insects have been observed to date.

COMPARISON WITH OTHER KNOW VARIETIES

The closest known variety to 'Kakegawa AU3' is the variety 'Wildside', a plant described and illustrated in U.S. Plant Pat. No. 10,603. The following table compares the differences that distinguish the new variety from the similar variety 'Wildside'.

| Characteristic | 'Kakegawa AU3' | 'Wildside' |
|---|---|---|
| Flower diameter (cm) | 5.5 cm to 6.0 cm | 5.4 cm |
| Petal number | 21–22 | 14–17 |
| Petal width (mm) | 6–7 | 8–9 |

I claim:

1. A new and distinct plant of the Compositae family, *Osteospermum fruticosum* (L.) Norl., herein referred to by the name 'Kakegawa AU3', as illustrated and described.

* * * * *